US012004761B2

(12) United States Patent
Singleton et al.

(10) Patent No.: US 12,004,761 B2
(45) Date of Patent: Jun. 11, 2024

(54) THROMBOSIS MACERATING DEVICES FOR BLOOD VESSELS

(71) Applicant: Merit Medical Systems, Inc., South Jordan, UT (US)

(72) Inventors: Alex Singleton, Sandy, UT (US); Andrew S. Hansen, Bluffdale, UT (US); Clark Ragsdale, Herriman, UT (US); Kenneth Sykes, Bluffdale, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 18 days.

(21) Appl. No.: 16/776,336

(22) Filed: Jan. 29, 2020

(65) Prior Publication Data

US 2020/0246029 A1    Aug. 6, 2020

Related U.S. Application Data

(60) Provisional application No. 62/799,370, filed on Jan. 31, 2019, provisional application No. 62/879,294, filed on Jul. 26, 2019.

(51) Int. Cl.
*A61B 17/221* (2006.01)
*A61B 17/00* (2006.01)
*A61B 17/22* (2006.01)

(52) U.S. Cl.
CPC .. *A61B 17/221* (2013.01); *A61B 2017/00778* (2013.01); *A61B 2017/00871* (2013.01);
(Continued)

(58) Field of Classification Search
CPC ........ A61B 17/22031; A61B 17/22032; A61B 17/221; A61B 17/32; A61B 17/3207; A61B 17/320758; A61B 2017/00778; A61B 2017/00871; A61B 2017/00876; A61B 2017/22038; A61B 2017/22084;
(Continued)

(56) References Cited

U.S. PATENT DOCUMENTS

| 532,145 A | 1/1895 | Defatsch |
| 3,049,018 A | 8/1962 | Lusskin |

(Continued)

FOREIGN PATENT DOCUMENTS

| WO | 200117587 | 3/2001 |
| WO | 2018148456 | 8/2018 |

OTHER PUBLICATIONS

Oval English Definition and Meaning, Lexico.com, accessed Apr. 6, 2022 at https://www.lexico.com/en/definition/oval, copyright 2022 Lexico.com (Year: 2022).*

(Continued)

*Primary Examiner* — Kankindi Rwego
(74) *Attorney, Agent, or Firm* — Dorsey & Whitney LLP (57) ABSTRACT

A thrombosis macerating device for macerating blood clots and blockages in a blood vessel is disclosed. The macerating device comprises an expandable basket that is rotated to macerate the clot or blockage. The expandable basket is disposed at the distal end of the tubular shaft. The expandable basket comprises a plurality of struts that form a braiding pattern. The braiding pattern of the expandable basket comprises a pick per inch that ranges from 2 to 5.

14 Claims, 8 Drawing Sheets

(52) U.S. Cl.
CPC ............ *A61B 2017/00876* (2013.01); *A61B 2017/22038* (2013.01); *A61B 2017/22084* (2013.01)

(58) Field of Classification Search
CPC .... A61B 2017/2212; A61B 2017/2215; A61B 2017/2217; A61B 2017/320004; A61B 2017/320008; A61B 2017/320012; A61B 2017/320775; A61B 2017/32096; A61B 34/20; A61B 34/30; A61B 34/73; A61B 2034/301; A61B 2034/302; A61B 2034/303; A61B 2034/304; A61B 2034/731; A61B 2034/732; A61B 2034/733; A61B 17/32002; A61B 17/320725; A61B 17/32075
USPC ...................................................... 606/200
See application file for complete search history.

(56) References Cited

U.S. PATENT DOCUMENTS

| | | | |
|---|---|---|---|
| 3,416,531 A | 12/1968 | Lowell | |
| 4,524,650 A | 6/1985 | Marks | |
| 4,527,650 A | 6/1985 | Bartholet | |
| 4,885,003 A * | 12/1989 | Hillstead | A61B 17/320725 604/22 |
| 5,057,092 A | 10/1991 | Webster | |
| 5,071,425 A | 12/1991 | Gifford et al. | |
| 5,213,015 A | 5/1993 | Disston, Jr. | |
| 5,383,852 A * | 1/1995 | Stevens-Wright | A61M 25/0136 604/95.04 |
| 5,702,373 A | 12/1997 | Samson | |
| 5,927,345 A * | 7/1999 | Samson | A61M 39/08 138/123 |
| 6,066,149 A * | 5/2000 | Samson | A61B 17/221 606/127 |
| 6,375,615 B1 | 4/2002 | Flaherty et al. | |
| 6,454,779 B1 | 9/2002 | Taylor | |
| 7,037,316 B2 | 5/2006 | McGuckin, Jr. et al. | |
| 7,220,269 B1 | 5/2007 | Ansel et al. | |
| 8,764,779 B2 | 7/2014 | Levine et al. | |
| 8,808,237 B2 | 8/2014 | Thielen et al. | |
| 8,845,621 B2 | 9/2014 | Fojtik | |
| 2001/0031981 A1 | 10/2001 | Evans et al. | |
| 2002/0029052 A1 | 3/2002 | Evans et al. | |
| 2002/0151918 A1 | 10/2002 | Lafontaine et al. | |
| 2002/0169414 A1 | 11/2002 | Kletschka | |
| 2003/0040704 A1 | 2/2003 | Dorros et al. | |
| 2003/0055445 A1 | 3/2003 | Evans et al. | |
| 2005/0268750 A1 | 12/2005 | Bruce et al. | |
| 2007/0208361 A1 | 9/2007 | Okushi et al. | |
| 2008/0033467 A1 | 2/2008 | Miyamoto et al. | |
| 2008/0082107 A1 * | 4/2008 | Miller | A61B 17/221 606/127 |
| 2008/0125798 A1 | 5/2008 | Osborne et al. | |
| 2008/0234722 A1 | 9/2008 | Bonnette et al. | |
| 2008/0277445 A1 | 11/2008 | Zergiebel | |
| 2009/0030274 A1 | 1/2009 | Goldfarb et al. | |
| 2010/0023033 A1 | 1/2010 | Mauch et al. | |
| 2010/0249817 A1 * | 9/2010 | Mark | A61B 17/32002 606/170 |
| 2011/0082490 A1 * | 4/2011 | Connelly | A61M 29/02 606/194 |
| 2012/0059356 A1 | 3/2012 | Di Palma et al. | |
| 2012/0239008 A1 | 9/2012 | Fojtik | |
| 2012/0277671 A1 | 11/2012 | Fuentes | |
| 2012/0316586 A1 | 12/2012 | Demarais et al. | |
| 2013/0289578 A1 | 10/2013 | Noriega et al. | |
| 2014/0142594 A1 | 5/2014 | Fojtik | |
| 2014/0228869 A1 | 8/2014 | Bonnette et al. | |
| 2014/0277015 A1 | 9/2014 | Stinis | |
| 2015/0305765 A1 | 10/2015 | Fojtik | |
| 2015/0374483 A1 * | 12/2015 | Janardhan | B23K 26/1435 606/200 |
| 2016/0015505 A1 | 1/2016 | Johnson et al. | |
| 2016/0038174 A1 | 2/2016 | Bruzzi et al. | |
| 2016/0066933 A1 | 3/2016 | Root et al. | |
| 2016/0270813 A1 | 9/2016 | Chida | |
| 2016/0331468 A1 | 11/2016 | Lee et al. | |
| 2017/0020556 A1 * | 1/2017 | Sutton | A61B 17/320725 |
| 2017/0238960 A1 | 8/2017 | Hatta et al. | |
| 2017/0252057 A1 | 9/2017 | Bonnette et al. | |
| 2018/0042628 A1 * | 2/2018 | Panian | A61F 2/013 |
| 2018/0126119 A1 | 5/2018 | Mcniven et al. | |
| 2018/0235652 A1 * | 8/2018 | Benjamin | A61B 17/320725 |
| 2018/0242989 A1 | 8/2018 | Nita | |
| 2018/0271556 A1 | 9/2018 | Bruzzi et al. | |
| 2020/0078029 A1 | 3/2020 | Hansen | |
| 2021/0077133 A1 | 3/2021 | Singleton et al. | |

OTHER PUBLICATIONS

International Search Report and Written Opinion dated Jan. 3, 2020 for PCT/UA2019/049974.
International Search Report and Written Opinion dated Jan. 6, 2017 for PCT/US2016/053932.
Notice of Allowance dated Sep. 11, 2019 for U.S. Appl. No. 15/277,473.
Office Action dated Apr. 22, 2019 for U.S. Appl. No. 15/277,473.
Office Action dated Nov. 29, 2018 for U.S. Appl. No. 15/277,473.
SPINR Product Brochure, Rights acquired by Merit Medical Systems, Inc. ,Jul. 2015.
International Search Report and Written Opinion dated Jun. 1, 2020 for PCT/US2020/015721.
International Search Report and Written Opinion dated Mar. 23, 2021 for PCT/US2020/051270.
Office Action dated Apr. 15, 2021 for U.S. Appl. No. 16/563,390.
Office Action dated Aug. 25, 2021 for U.S. Appl. No. 16/563,390.
Office Action dated Mar. 2, 2023 for U.S. Appl. No. 17/024,297.
Office Action dated Apr. 7, 2022 for U.S. Appl. No. 17/024,297.
Office Action dated Oct. 25, 2022 for U.S. Appl. No. 17/024,297.
Office Action dated Sep. 21, 2023 for U.S. Appl. No. 17/024,297.

* cited by examiner

THROMBOSIS MACERATING DEVICES FOR BLOOD VESSELS

RELATED APPLICATIONS

This application claims priority to U.S. Provisional Application No. 62/799,370, filed on Jan. 31, 2019 and titled, "Thrombosis Macerating Devices for Blood Vessels," and U.S. Provisional Application No. 62/879,294, filed on Jul. 26, 2019 and titled, "Thrombosis Macerating Devices for Blood Vessels," both of which are hereby incorporated by reference in their entireties.

TECHNICAL FIELD

The present disclosure relates generally to the field of medical devices. More particularly, some embodiments relate to apparatuses and methods for macerating a clot from a patient's vascular system.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

The fields of interventional radiology, vascular surgery, and cardiology may include the macerating of clots and the removal of clots in the arterial and venous systems to reduce complications arising from vascular occlusions. Additionally, thrombosis of hemodialysis access grafts/fistulae is an issue that dialysis patients encounter wherein treatment may include clot removal. In the case of deep vein thrombosis (DVT), a disease state in which a patient has a blood clot in a peripheral vein, the clot may be removed to resolve the patient's acute symptoms or to help prevent complications of the DVT, including valve damage, Post Thrombotic Syndrome, or embolization/migration of the clot to the lung, a potentially fatal condition called pulmonary embolism (pulmonary artery occlusion). These clots may be removed via surgical, pharmacological, or minimally invasive mechanical or pharmacomechanical means. Techniques used for treatment of the clot include injecting/infusing a thrombolytic agent, tissue plasminogen activator (tPA), into the clot to help dissolve the clot, or alternative methods, including mechanical removal of the clot using aspiration catheters, rotational baskets, or other mechanical maceration devices.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities, including mechanical, fluidic, and thermal interaction. Thus, two components may be coupled to each other even though they are not in direct contact with each other. The phrases "attached to" or "attached directly to" refer to interaction between two or more entities that are in direct contact with each other and/or are separated from each other only by a fastener of any suitable variety (e.g., mounting hardware or an adhesive). The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

Figure 1:
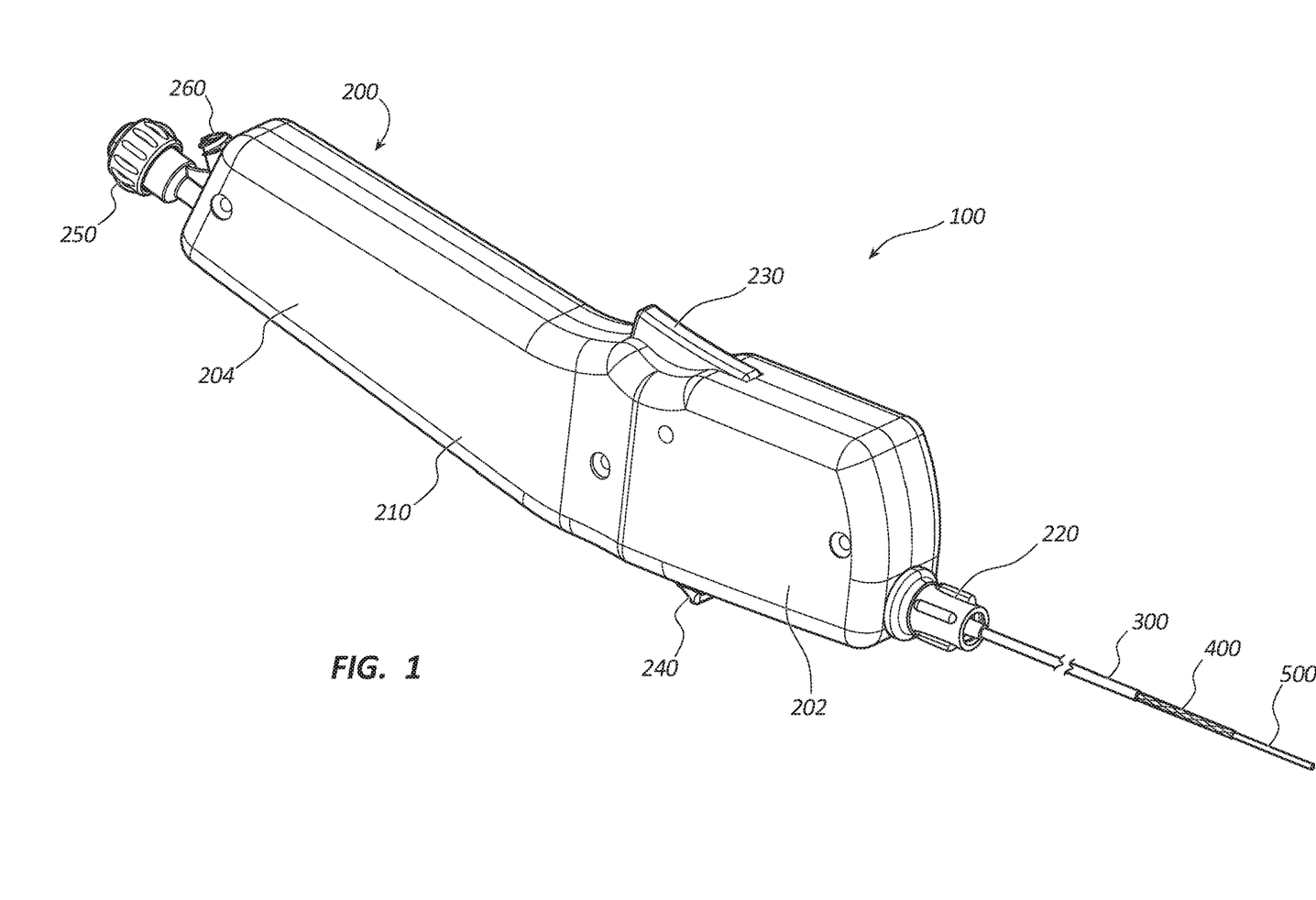
FIG. 1 shows a perspective view of a thrombosis macerating device comprising a handle and a catheter according to one embodiment.
Figure 2:
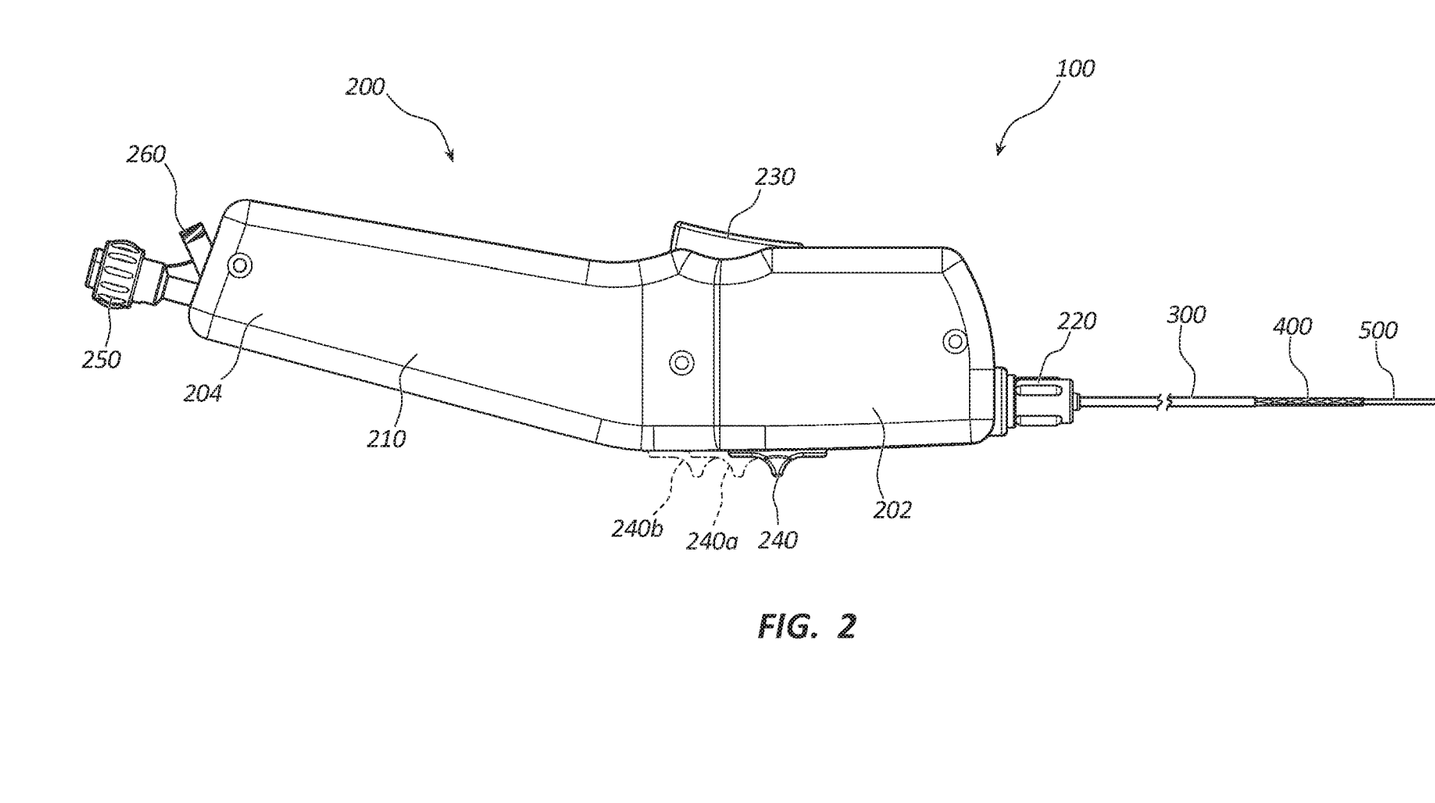
FIG. 2 shows a side view of the thrombosis macerating device of FIG. 1.

FIG. 1 illustrates a perspective view of a macerating device 100 that comprises a handle 200, a catheter 300, a macerating element 400, and a guidewire 500. FIG. 2 illustrates a side view of the macerating device 100. The macerating element 400 of the macerating device 100 may be configured to rotate to macerate and remove or displace a clot or blockage, such as in vascular thrombosis. In some embodiments, the macerating device 100 may be configured to macerate a clot or blockage into small components in the venous vasculature. In some such embodiments the macerated small components may be sufficiently small as reduce or minimize risk of pulmonary embolism.

The macerating element 400 may include an expandable basket 410 (see FIG. 4) that is configured to expand and collapse. In a collapsed configuration, the expandable basket 410 may be disposed within the catheter 300 and the catheter 300 may be deployed within the vasculature of a patient to a desired location to treat a blockage or clot. The expandable basket 410 may be expanded to an expanded configuration and rotated to macerate the desired blockage or clot. In some instances, the clot or blockage may be aspirated after being macerated.

The handle 200 may comprise a housing 210 for housing the various components of the macerating device 100. For example, the housing 210 may house a motor for rotating the expandable basket 410. The housing 210 may also house a power source to power the motor.

The handle 200 may further include a coupler 220. The catheter 300, the macerating element 400, and the guidewire 500 may be coupled to the handle 200 via the coupler 220. Embodiments where these components are removably coupled as well as embodiments wherein these elements are fixedly coupled are within the scope of this disclosure.

The handle 200 may further include a rotational speed control mechanism configured to control the rotational speed (or angular velocity) of the macerating element 400. The rotational speed control mechanism may be a trigger 230 disposed on a top surface of the handle 200. The trigger 230 may enable a user, such as a medical professional, to control the rotational speed of the macerating element 400, e.g., the expandable basket 410. In some embodiments, the trigger 230 may enable the user to variably control the rotational speed of the expandable basket 410. For example, the amount of pressure the user applies to the trigger 230 may determine the speed of the expandable basket 410. The more pressure applied to the trigger 230 by the user increases the rotational speed of the expandable basket 410.

The macerating device 100 may be configured to rotate the expandable basket 410 in a clockwise or a counterclockwise direction. In various embodiments, and in various procedures, the expandable basket 410 may rotate at various rotational speeds, including 0-10,000 rpm; 500-10,000 rpm; 500-2,500 rpm; and 1,000-5,000 rpm. Further, systems configured to rotate the expandable basket 410 at rotational speeds of at least 500 rpm; at least 1,000 rpm; at least 500 rpm and up to 10,000 rpm; less than 500 rpm; less than 250 rpm; and less than 200 rpm are also within the scope of this disclosure.

In some embodiments, the trigger 230 may be configured to rotate the expandable basket 410 at any number of predetermined rotational speeds. For example, the trigger 230 may be configured with set points correlating to a high speed, a medium speed, and a low speed. The trigger 230 may be configured, for example, with distinct regions that correlate to such set points. For example, a first region may correspond with a low speed, for example, 500 rpm to 5,000 rpm. A second region may correspond with a medium speed, for example, 1,000 rpm to 5,000 rpm. A third region may correspond with a high speed, for example, 1,000 rpm to 10,000 rpm.

In some embodiments, the trigger 230 may be configured with set points correlating to a high speed, a low speed, and an off configuration. The trigger 230 may be configured, for example, with distinct regions that correlate to such set points. For example, a first region may correspond with an off configuration wherein the expandable basket 410 does not rotate. A second region may correspond with a low speed, for example, 500 rpm to 5,000 rpm. A third region may correspond with a high speed, for example, 1,000 rpm to 10,000 rpm.

For example, in one embodiment, the annular velocity of the high speed may be 4,000 rpm and the angular velocity of the low speed may be 2,000 rpm. In another embodiment, the annular velocity of the high speed may be 8,000 rpm and the angular velocity of the low speed may be 4,000 rpm. In another embodiment, the annular velocity of the high speed may be 1,500 rpm and the angular velocity of the low speed may be 1,000 rpm. In another embodiment, the annular velocity of the high speed may be 4,000 rpm and the angular velocity of the low speed may be 3,000 rpm.

The handle 200 may further include a diameter control mechanism configured to control or change the diameter of the expandable basket 410. The diameter control mechanism may be a slider 240 operatively coupled to the expandable basket 410 such that displacement of the slider 240 variably alters the diameter of the expandable basket 410. In the illustrated embodiment, the slider 240 is configured to be displaced in a direction parallel to a longitudinal axis of the handle 200. In other embodiments, the slider 240 may be configured to be displaced in other directions. During a procedure, the user may manipulate the slider 240 to set, for example, a maximum diameter of the expandable basket 410. For example, during a procedure, the user may manipulate the slider 240 to lock the maximum diameter of the expandable basket 410 at a diameter that is less than the diameter of a target vessel to avoid damaging the vessel during the macerating procedure.

In some embodiments, the slider 240 may include a plurality of detents. The detents may lock the slider 240 in place until a predetermined amount of force is applied to the slider 240 to release it from the detent until it reaches the next detent. Each detent may correspond with a predetermined diameter of the expandable basket 410. In some embodiments, the predetermined diameter may correlate to a maximum diameter of the expandable basket 410. That is, in some embodiments, the expandable basket 410 may be compressible to a smaller diameter (due, for example, to external constraining forcing acting on the outside diameter of the expandable basket 410) though the position of the slider 240 controls the maximum size of expansion of the expandable basket 410. As one example, in one embodiment, the slider 240 may have three detents that correspond with a small diameter, a medium diameter, and a large diameter. FIG. 2 illustrates three possible positions of the slider 240. The slider 240 represents a first position or a small diameter, slider 240*a* represents a second position or a medium diameter, and slider 240*b* represents a third position or a large diameter. The small diameter may or may not correspond with the diameter of the expandable basket 410 in the collapsed configuration. In certain embodiments, the small diameter may be 5 mm, the medium diameter may be 10 mm, and the large diameter may be 15 mm.

The handle 200 may be designed to fit ergonomically within the hand of the user, thus the macerating device 100 may be configured as a handheld device. The handle 200 may include a distal portion 202 and a proximal portion 204. The proximal portion 204 may be angled relative to the distal portion 202, facilitating griping of the proximal portion 204 with the palm while positioning the hand to manipulate the trigger 230 and the slider 240 with the thumb and fingers. For example, the user could manipulate the trigger 230 with their thumb and manipulate the slider 240 with their index finger.

The handle 200 may further include a second port 250. The second port 250 may communicate with a lumen disposed within the macerating element 400. The second port 250 may be in communication with the lumen of the handle and in communication with a first port in the coupler 220. Thus, the user may advance an elongate component, such as the guidewire 500, through the second port 250 and the lumen of the handle 200 and through the first port. The elongate component may then extend into the lumen of the macerating element 400. Furthermore, the second port 250 may be in fluid communication with the lumen of the macerating element 400. In such instances, the second port 250 may function as an aspiration or infusion port for aspiration or infusion of materials, including aspiration of clots or other matter and/or infusion of medication, saline, etc. For example, the user may infuse a medication, such as tPA, to help break up the clot or blockage before the user attempts to macerate the clot or blockage. In some embodiments, a vacuum source may be applied to the second port 250 to aspirate the macerated clot or blockage.

The handle 200 may further include a third port 260. The third port 260 may be in communication with a second lumen, such as a lumen disposed within the catheter 300 between the macerating element 400 and the catheter 300. The third port 260 may also function as an aspiration or infusion port. In some embodiments, a vacuum source may be applied to the third port 260 to remove the macerated clot or blockage. In some embodiments, the user may infuse a medication, such as tPA, to help break up the clot or blockage.

Figure 3:
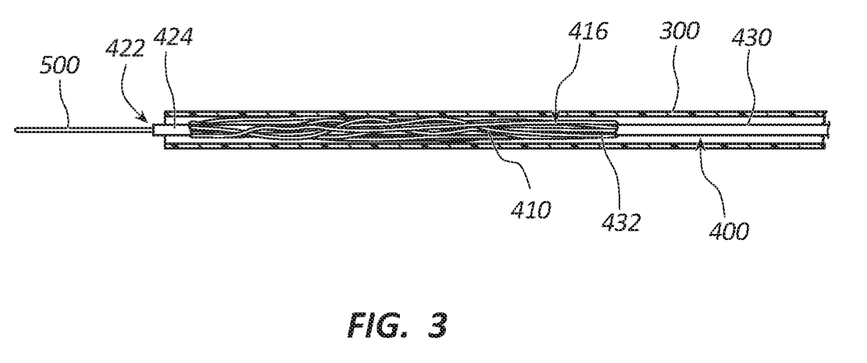
FIG. 3 shows a detailed view of an expandable basket of the macerating device in a collapsed configuration according to one embodiment.
Figure 4:
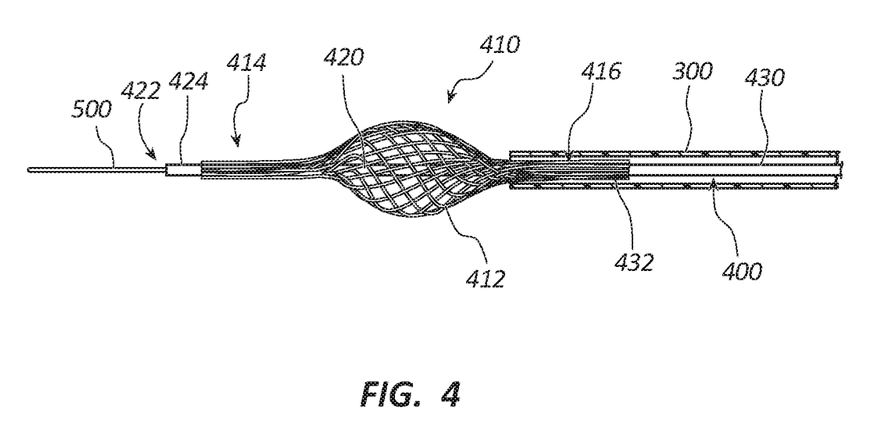
FIG. 4 shows a detailed view of the expandable basket of FIG. 3 in an expanded configuration.

FIGS. 3 and 4 illustrate a detailed view of the distal end of the catheter 300, the macerating element 400, and the guidewire 500. FIG. 3 illustrates the expandable basket 410 disposed within the catheter 300 with the expandable basket 410 in a collapsed configuration. FIG. 4 illustrates the expandable basket 410 disposed out of the catheter 300 with the expandable basket 410 in an expanded configuration.

In the illustrated embodiment, the macerating element 400 comprises the expandable basket 410, an inner inner tubular shaft 420, and an outer tubular shaft 430. In the illustrated embodiment, the outer tubular shaft 430 is coupled to the expandable basket 410 at a distal end 432 of the outer tubular shaft 430. Also in the illustrated embodiment, the inner inner tubular shaft 420 is disposed within the outer tubular shaft 430 and within the expandable basket 410 and is coupled to a distal end of the expandable basket 410. The outer tubular shaft 430 and the inner inner tubular shaft 420 may be configured to move relative to each other in the axial direction.

The inner inner tubular shaft 420 may include a lumen disposed within. The inner inner tubular shaft 420 may include an opening 422 disposed at a distal end 424 of the inner inner tubular shaft 420 that is in communication with the lumen. The guidewire 500 may be advanced through the handle 200 and through the lumen of the inner inner tubular shaft 420. As discussed previously, the lumen in the inner inner tubular shaft 420 may be used for aspiration and/or infusion, including for medication, saline, clots etc.

The macerating element 400 may further include a second lumen. The second lumen may be disposed between the inner inner tubular shaft 420 and the outer tubular shaft 430, in other words, the second lumen may comprise an annular space between the inner inner tubular shaft 420 and the outer tubular shaft 430. As discussed previously, the second lumen may be used for infusion or aspiration. The second lumen may be in fluid communication with the third port 260 and may be used for aspiration and/or infusion.

In some embodiments, a third lumen may be disposed between the outer tubular shaft 430 and the catheter 300. This lumen may also be used for aspiration and/or infusion. In some embodiments, the third lumen may be in fluid communication with the third port 260 in addition to, or instead of, communication between the third port 260 and the second lumen. In some embodiments, the third lumen may be in fluid communication with a fourth port (not shown). In such embodiments, the second lumen and the third lumen may be separately used for aspiration and/or infusion.

As shown in the figures, the expandable basket 410 may comprise a plurality of struts 412. In the illustrated embodiment, each strut 412 extends from a proximal end 414 of the expandable basket 410 to a distal end 416 of the expandable basket 410. The expandable basket 410 is coupled to the outer tubular shaft 430 at the proximal end 414 of the expandable basket 410 and the distal end 432 of the outer tubular shaft 430. The expandable basket 410 is also coupled to the inner tubular shaft 420 at the distal end 416 of the expandable basket 410 and the distal end 424 of the inner tubular shaft 420.

The expandable basket 410 may be collapsed and expanded in a number of different ways. For example, the struts 412 of the expandable basket 410 may be made of a memory material, such as Nitinol, so that expandable basket 410 may achieve a predetermined shape when the expandable basket 410 is unsheathed. The catheter 300 may sheath the expandable basket 410 and apply the appropriate amount of pressure to the expandable basket 410 to keep the expandable basket 410 in the collapsed configuration when the expandable basket 410 is disposed within the catheter 300. The unsheathing may occur when the expandable basket 410 is either advanced out of the catheter 300 or when the catheter 300 is drawn back, enabling the expandable basket 410 to expand to its expanded predetermined configuration.

In another embodiment, axial movement of the inner tubular shaft 420 relative to the outer tubular shaft 430 may expand and collapse the expandable basket 410. As discussed previously, the proximal end 414 of the expandable basket 410 may be coupled to the distal end 432 of the outer tubular shaft 430 and the proximal end 414 of the expandable basket 410 may be coupled to the distal end 424 of the inner tubular shaft 420. In such embodiments, distal displacement of the outer tubular shaft 430 relative to the inner tubular shaft 420 may be configured to exert a longitudinal compressive force on the struts 412 and expand the expandable basket 410. Similarly, proximal displacement of the outer tubular shaft 430 relative to the inner tubular shaft 420 may be configured to collapse the expandable basket 410.

In another embodiment, a proximally oriented force applied to the inner tubular shaft 420 may be configured to displace the inner tubular shaft 420 proximally relative to the outer tubular shaft 430 and expand the expandable basket 410. Similarly, a distally oriented force applied to the inner tubular shaft 420 may be configured to displace the inner tubular shaft 420 distally relative to the outer tubular shaft 430 and collapse the expandable basket 410.

For some embodiments, in the collapsed configuration, the diameter of the expandable basket 410 may range from 1 mm to 5 mm. Further, for some such embodiments, in an expanded configuration, the diameter of the expandable basket 410 may range from 5 mm to 30 mm. Additionally, in some embodiments, the expandable basket 410 may comprise 16 struts 412 as shown in the figures, or may comprise more or fewer than 16 struts, including odd and even numbers of struts. For example, the number of the struts may be 6, 8, 12, 15, 16, 18, etc. The number of struts may also range between 6 struts and 24 struts or 12 struts to 18 struts.

Figure 5:
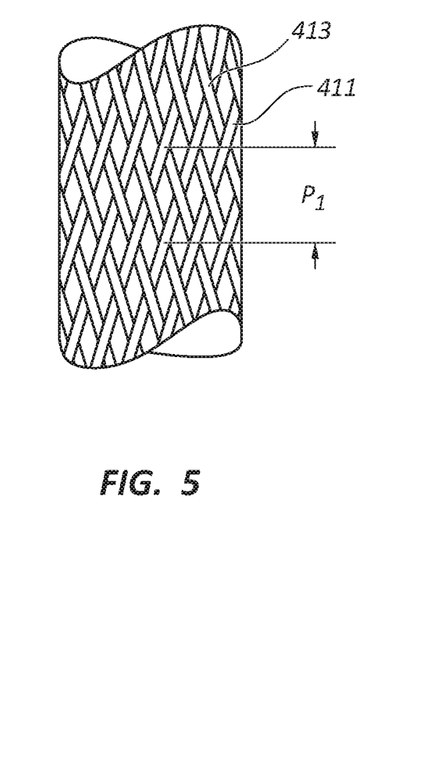
FIG. 5 shows a half load braiding pattern of an expandable basket according to one embodiment.

The expandable basket 410 may be formed by braiding the plurality of struts 412 in a braiding pattern. The expandable basket 410 may be manufactured on a braid machine by using various braiding patterns. FIG. 5 illustrates a half load pattern in which a single weft strut 411 alternately passes under then over warp struts 413. In the braid pattern, the weft struts 411 and warp struts 413 rotate about the center axis in opposite directions.

Figure 6:
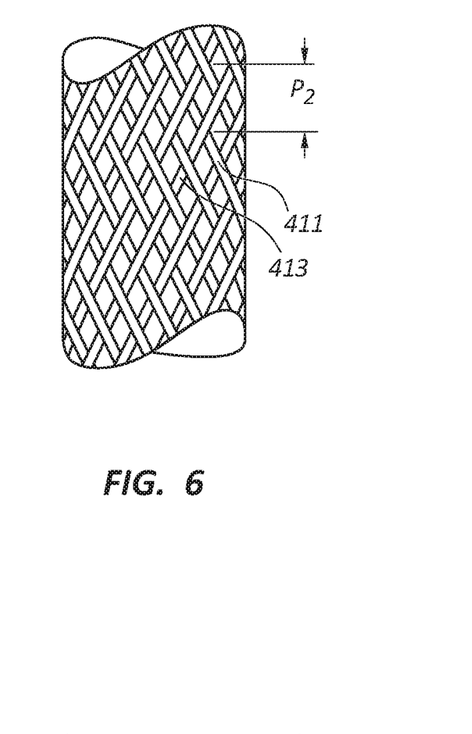
FIG. 6 shows a full load braiding pattern of an expandable basket according to one embodiment.

FIG. 6 illustrates a full load pattern in which a single weft strut 411 passes under two warp struts 413 and then over two warp struts 413. The weft struts 411 and the warp struts 413 rotate in opposite directions.

Figure 7:
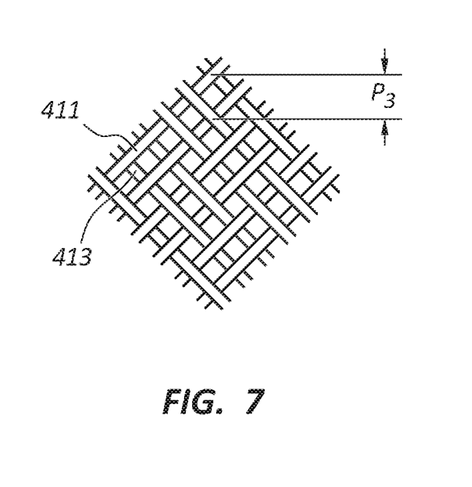
FIG. 7 shows a diamond braiding pattern of an expandable basket according to one embodiment.

FIG. 7 illustrates a diamond pattern in which two weft struts 411 side by side alternately pass under two warp struts 413 and then pass over two warp struts 413. These weft struts 411 and the warp struts 413 rotate in opposite directions.

The radial force achieved by the expandable basket 410 during rotation is partially based on several variables. One of the variables that partially determines the maximum radial force achieved by the expandable basket 410 is the braiding pattern of the expandable basket 410. As discussed previously, various braiding patterns may be implemented, such as full load, half load, and diamond, and the braiding pattern may significantly change the radial force achieved by the expandable basket 410.

For example, Table 1, reproduced below, lays out the unexpected results achieved by an expandable basket with a half load braiding pattern versus a full load braiding pattern. Table 1 compares the maximum radial force achieved by the expandable basket in four different configurations. The four different configurations are 3×10 stainless steel full load braiding pattern, 3×10 stainless steel half load braiding pattern, 4×12 Nitinol full load braiding pattern, and 4×12 Nitinol half load braiding pattern. The variables specifically tested in these experiments were full load versus half load and stainless steel versus Nitinol. The dimensions listed (3×10 and 4×12) refer to the dimensions of the struts. For example, 3×10 refers to a flattened strut that comprises round edges. The strut may have a height that is around 3 thousandths inches and may have a width that is around 10 thousandths inches. 4×12 refers to a flattened strut that comprises round edges. The strut may have a height that is around 4 thousandths inches and may have a width that is around 12 thousandths inches. Additional details in regard to the struts are disclosed below in regard to FIG. 9.

The experiments were performed for 60 seconds and the expandable basket began with a diameter around 11 mm. The expandable basket was then compressed to a diameter of around 6 mm. The expandable basket was then expanded to around 11 mm. The maximum radial force achieved by the expandable basket calculated in Newtons (N) for each configuration is reproduced in Table 1.

Figure 8:
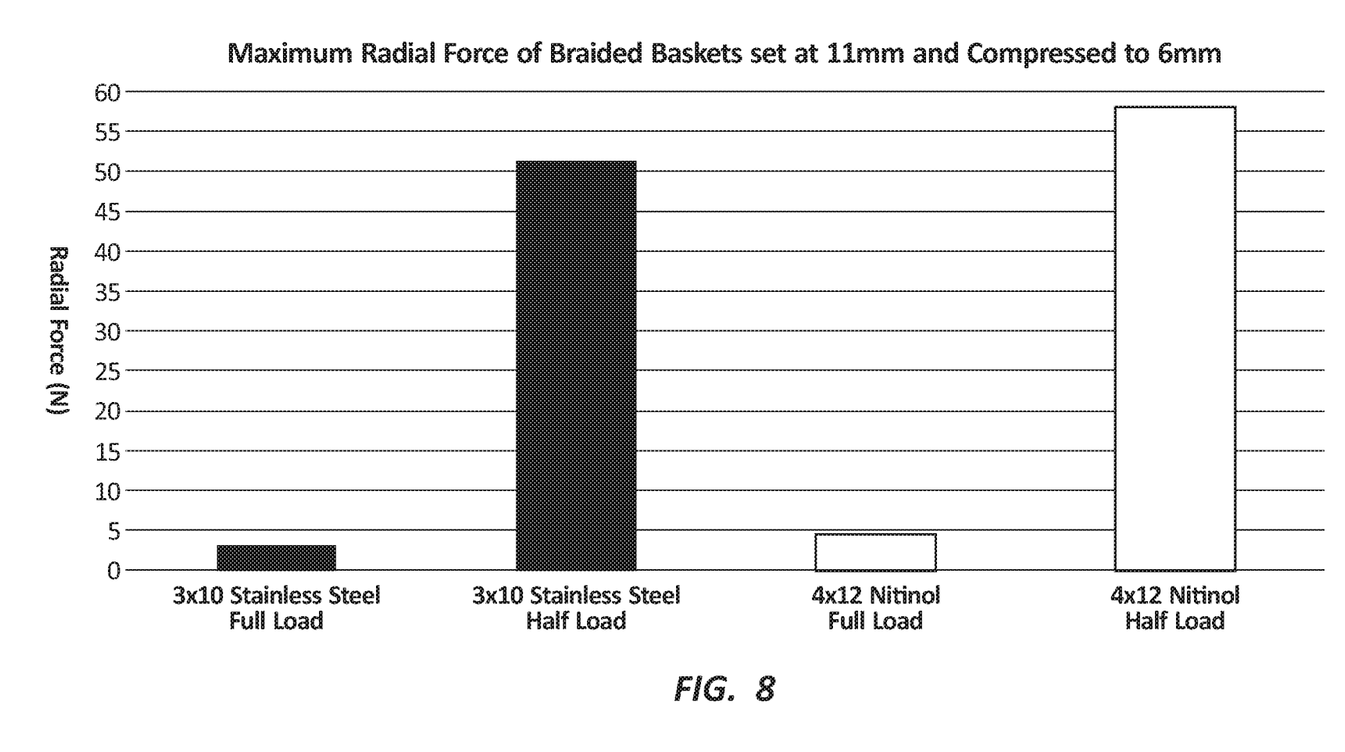
FIG. 8 shows a graph of the maximum radial force produced by half load and full load of a braided expandable baskets.

FIG. 8 illustrates a bar graph of the data in Table 1. The data proves that a half load braiding pattern achieves a maximum radial force that is at least 12 times greater than the full load braiding pattern. A stainless steel half load braiding pattern achieved maximum radial force that was 16 times greater than the stainless steel full load braiding pattern. The Nitinol half load braiding pattern achieved a maximum radial force that was at least 12 times greater than the Nitinol full load braiding pattern. It was expected that the maximum radial force of the different braiding patterns would be different; however, it was completely unexpected that the half load would provide a 12-time increase in maximum radial force.

Other variables that may partially determine the maximum radial force include but are not limited to: the dimensions of the struts, the material of the struts, the diameter of the expandable basket, picks per inch of the braiding pattern (discussed in more detail below), etc. Various combinations of these variables may lead to higher maximum radial forces by the expandable basket.

The diameter of the expandable basket 410 is determined by the picks per inch (PPI) of the braiding pattern. PPI is defined by the number of weft struts 411 per inch. FIGS. 5, 6, and 7 each illustrate a single pick: P1, P2, and P3. In some embodiments, the PPI of the expandable basket 410 may range between 2 and 10. In some embodiments, the PPI of the expandable basket 410 may range between 2 and 5. The smaller the PPI of the expandable basket 410, the larger the diameter of the expandable basket 410 in the expanded configuration. For example, a PPI of 4 may achieve a diameter of 15 mm, and a PPI of 3.5 may achieve a diameter of 20 mm.

The PPI of the braiding pattern also determines the radial force achieved by the expandable basket 410 during rotation. The lower the PPI, the lower the radial force. Higher radial forces help achieve better maceration of the clot or blockage.

Figure 9:
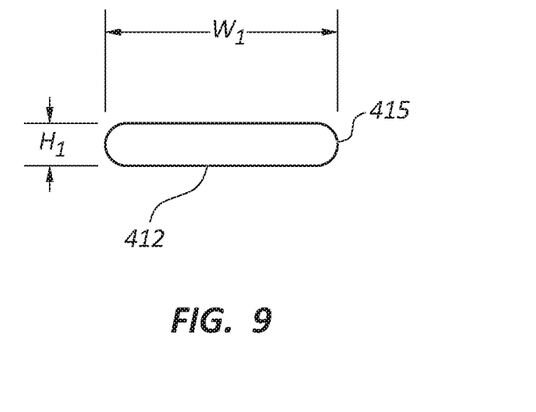
FIG. 9 shows a cross-sectional view of a strut of an expandable basket according to one embodiment.

In some embodiments, the struts 412 are drawn round and then flattened. FIG. 9 illustrates a cross-sectional view of a single strut 412 in the flattened configuration. The flattened strut 412 comprises round edges 415. The strut 412 may have a height H1 that is around 3 thousandths inches and may have a width W1 that is around 10 thousandths inches. The greater the height H1 of the strut 412 the greater the radial force. The lesser the height H1 of the strut 412 the sharper the strut 412.

In some embodiments, the expandable basket 410 and the outer tubular shaft 430 may be formed from the same plurality of the struts 412. The outer tubular shaft 430 and the expandable basket 410 may comprise the same braiding pattern but have different PPIs. In some embodiments, the PPI of the outer tubular shaft 430 may transition to the PPI of the expandable basket 410 at a transition point. The transition point may coincide with the distal end 432 of the outer tubular shaft 430. The PPI of the outer tubular shaft 430 may range from 16 to 40 while the PPI of the expand-

TABLE 1

Maximum Radial Force of Braided Baskets Set at 11 mm and Compressed to 6 mm

| Configuration | 3 × 10 Stainless Steel Full Load | 3 × 10 Stainless Steel Half Load | 4 × 12 Nitinol Full Load | 4 × 12 Nitinol Half Load |
| --- | --- | --- | --- | --- |
| Maximum Radial Force (N) | 3.12 | 51.40 | 4.52 | 58.06 | able basket 410 may range from 2 to 10. In some embodiments, the PPI of the outer tubular shaft 430 may range between 18 and 22.

In some embodiments, the expandable basket 410 may be made of a memory material, such as Nitinol, and may be heat treated so that the PPI of the expandable basket 410 is maintained.

Figure 10:
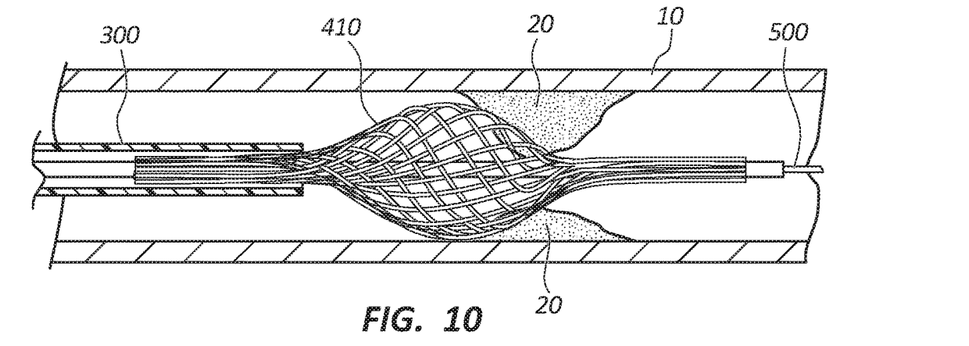
FIG. 10 shows a macerating device with an expanded basket being rotated in a partially occluded vessel.

The macerating element 400 may be used in partially occluded and fully occluded vessels. FIG. 10 illustrates the macerating element 400 disposed in a patient's vessel 10, the vessel 10 being partially occluded by a clot or blockage 20. The expandable basket 410 may be advanced out of the catheter 300 and positioned near the clot or blockage 20. The expandable basket 410 may be expanded and rotated to macerate the clot or blockage 20. The diameter of the expandable basket 410 may be set by the user and may be based on the size of the vessel 10. The size of the vessel 10 may be determined before the procedure is performed via imaging or may be determined during the procedure via imaging or by resistance and feel as the basket 410 is expanded. After the clot or blockage 20 is macerated, the expandable basket 410 may be collapsed and retracted into the catheter 300. The catheter 300 may then be removed from the patient's vasculature.

Figure 11:
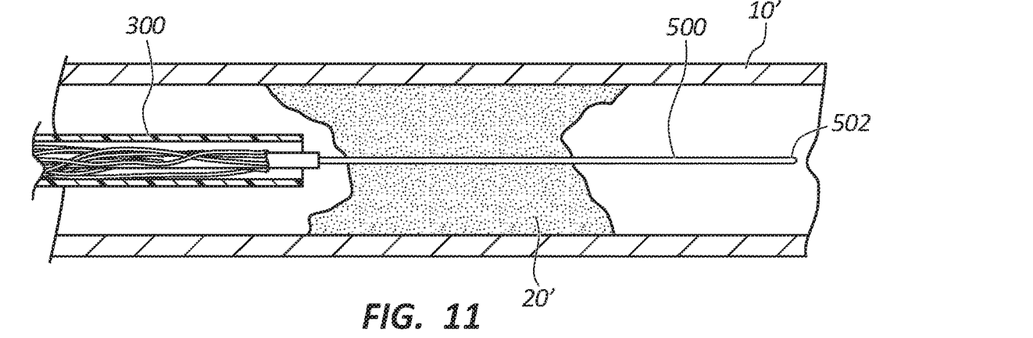
FIG. 11 shows a macerating device disposed near a fully occluded vessel of a patient with a guidewire of the macerating device puncturing the blockage and an expandable basket in a collapsed configuration disposed within a catheter of the macerating device.
Figure 12:
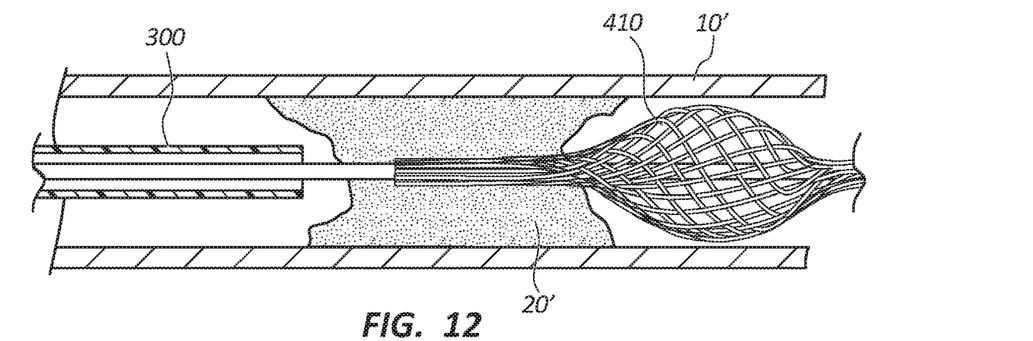
FIG. 12 shows the macerating device of FIG. 10 with the expandable basket of the macerating device puncturing the blockage and expanded to an expanded configuration.
Figure 13:
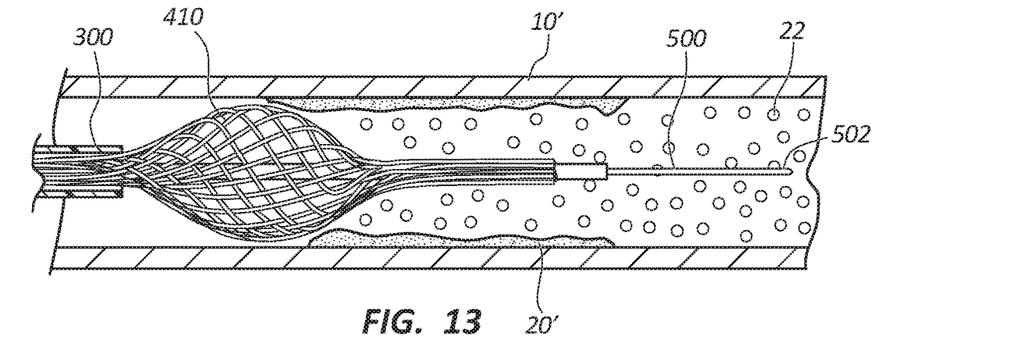
FIG. 13 shows the macerating device of FIGS. 10 and 11 with the expandable basket in the expanded configuration macerating the blockage and being pulled toward the catheter of the macerating device.

FIGS. 11-13 illustrate the process of macerating a clot or blockage 20' that fully occludes the patient's vessel 10'. FIG. 11 illustrates a distal tip 502 of the guidewire 500 puncturing the clot or blockage 20' until it completely punctures the clot or blockage 20'.

Once the guidewire 500 has completely punctured the clot or blockage 20', the expandable basket 410 may be advanced out of the catheter 300 and through the clot or blockage 20' via the path created by the guidewire 500, as illustrated in FIG. 12. Once on the other side of the clot or blockage 20', the expandable basket 410 may be expanded and rotated to macerate the clot or blockage 20'. The diameter of the expandable basket 410 may be set by the user and may be based on the size of the vessel 10'. The size of the vessel 10' may be determined before the procedure is performed via imaging or may be determined during the procedure via imaging.

FIG. 13 illustrates the expandable basket 410 macerating the clot or blockage 20' via rotation of the expandable basket 410. The clot or blockage 20' may be macerated into a plurality of pieces 22 that may be either aspirated or left in the vessel 10'. The expandable basket 410 is configured to macerate the clot or blockage 20' into the pieces 22 that are small enough that they will not adversely affect the patient. The expandable basket 410 may be pulled toward the catheter 300. After the clot or blockage 20' is macerated, the expandable basket 410 may be collapsed and retracted into the catheter 300. The catheter 300 may then be removed from the patient's vasculature.

In another embodiment, the process depicted in FIGS. 11-13 may be reversed. The expandable basket 410 may be expanded then pushed through the clot or blockage 20' to macerate the clot or blockage 20' rather than pushing the expandable basket 410 through the clot or blockage 20' before expanding and pulling the expandable basket 410 toward the catheter 300 to macerate the clot or blockage 20'.

In some embodiments, the handle 200 may provide a visual or tactile feedback to the user to indicate when the expandable basket 410 is macerating the clot or blockage 20. For example, when the expandable basket 410 is disposed in the clot or blockage 20, the motor may experience an increase in torque or resistance. Accordingly, a sensor may detect this increase in torque or resistance and provide feedback to the user to indicate that the expandable basket 410 is disposed within the clot or blockage 20. This feedback may be tactile (vibration of the handle 200) or visual (LEDs disposed in the housing 210 of the handle 200).

Figure 14:
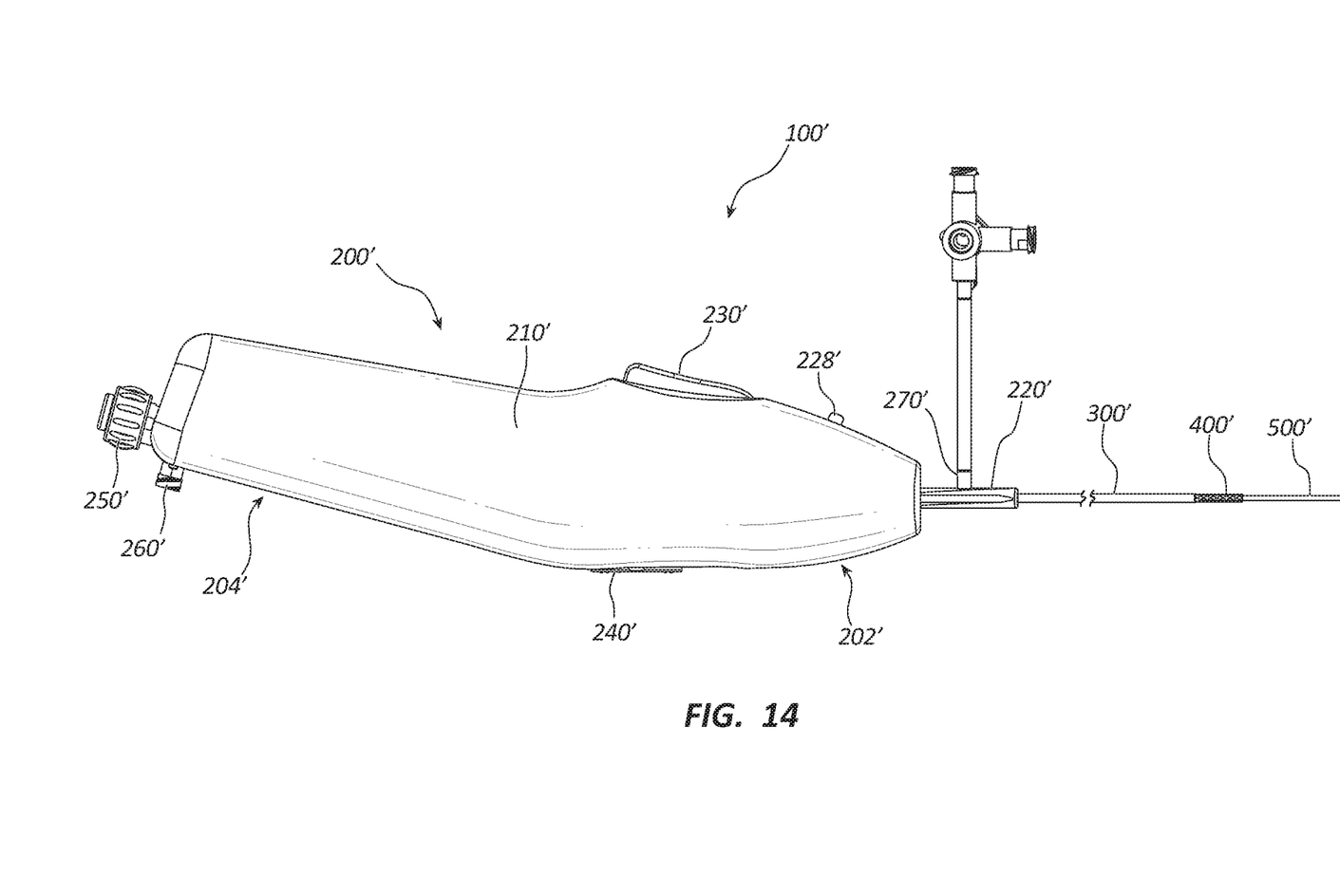
FIG. 14 shows a perspective view of a thrombosis macerating device comprising a handle and a catheter according to one embodiment.
Figure 15:
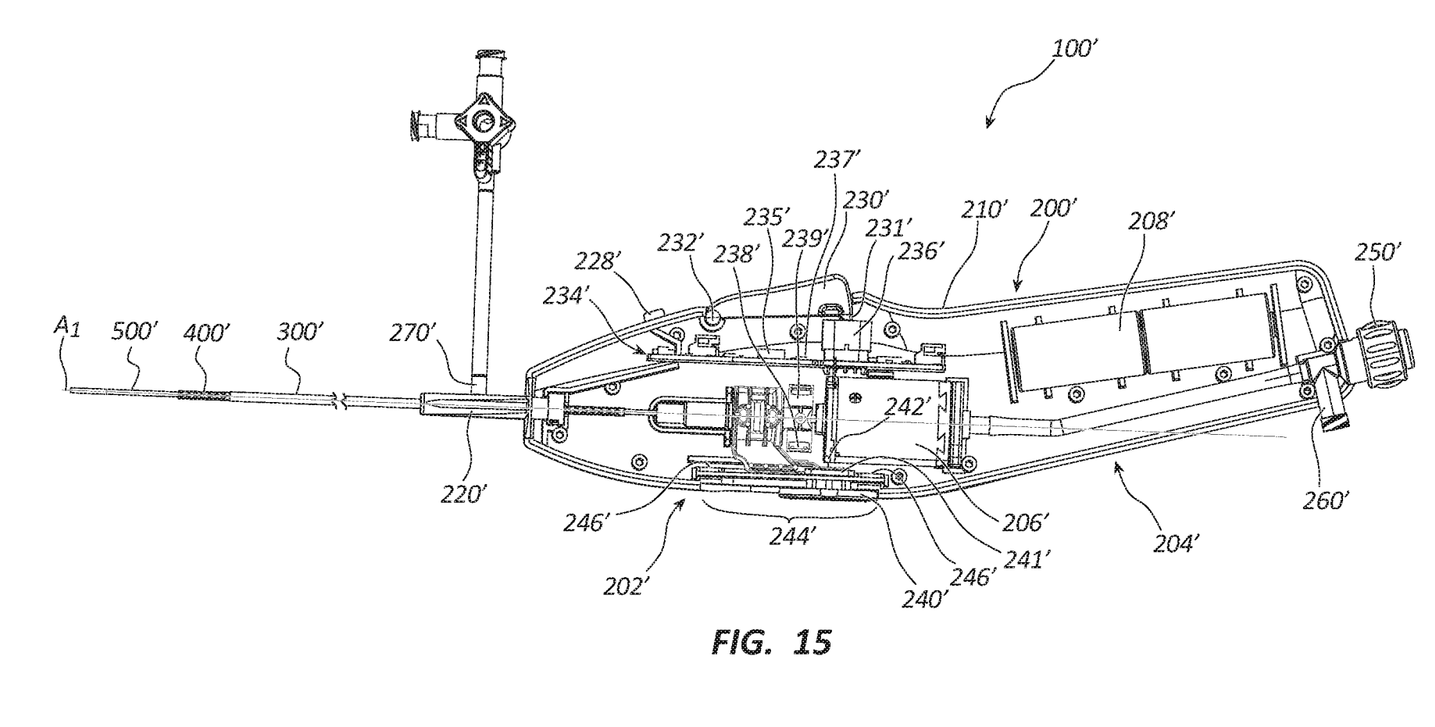
FIG. 15 shows a cross-sectional view of the thrombosis macerating device of FIG. 14.

FIGS. 14 and 15 depict an embodiment of a handle that resembles the macerating device 100 described above in certain respects. Accordingly, like features are designated with like reference numerals and an added apostrophe. For example, the embodiment depicted in FIGS. 14 and 15 includes a handle 200' that may, in some respects, resemble the handle 200 of FIGS. 1 and 2. Relevant disclosure set forth above regarding similarly identified features thus may not be repeated hereafter. Moreover, specific features of the macerating device 100 and related components shown in FIGS. 1 and 2 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the macerating device 100' and related components depicted in FIGS. 14 and 15. Any suitable combination of the features, and variations of the same, described with respect to the macerating device 100 and related components illustrated in FIGS. 1 and 2 can be employed with the macerating device 100' and related components of FIGS. 14 and 15, and vice versa.

FIG. 14 illustrates a perspective view of a macerating device 100'. The macerating device 100' includes a handle 200'. The handle 200' may comprise a housing 210' for housing the various components of the macerating device 100'.

FIG. 15 illustrates a cross-sectional view of the handle 200'. As discussed above, the housing 210' of the handle 200' may be configured to house or contain various components of the macerating device 100'. The housing comprises a distal portion 202' and a proximal portion 204'. A motor 206' may be disposed within the handle 200' in the distal portion 202' of the handle 200'. The motor 206' is configured to rotate the expandable basket. A power source 208' may be disposed in the proximal portion 204' of the handle 200'.

The handle 200' may further comprise a rotational speed control mechanism configured to control the rotational speed (or angular velocity) of the macerating element 400'. For example, the control mechanism may be configured to allow a user to control the speed of the macerating element 400'. The rotational speed control mechanism may be a trigger 230' disposed on a top surface of the handle 200'. The trigger 230' may be configured to control the rotational speed of the macerating element 400' in response to input from a user's finger or other portion of the users hand.

In the illustrated embodiment, the rotational speed control mechanism further comprises internal circuitry 234', such as a printed circuit board, disposed within the handle 200'. The trigger 230' is configured to engage with the internal circuitry 234'. The internal circuitry 234' may comprise a processor 235' for communicating with the motor 206' and controlling the rotational speed produced by the motor 206'.

The internal circuitry 234' may further comprise a button 236' for controlling the rotational speed produced by the motor 206'. The button 236' may comprise a plurality of configurations. Exemplary configurations may include off, low, and high. However, the button 236' may comprise more or fewer than these three configurations. In the illustrated embodiment, the button 236' is engageable with the trigger 230' and enables the user to manipulate the button 236' to one of the three different configurations. The trigger 230' may comprise a projection 231' that pivots about a pivot point 232'. When the user compresses the trigger 230', the trigger 230' may thus rotate about the pivot point 232' such that the projection 231' compresses the button 236'. The handle 200' may be configured such that each time the user compresses the trigger 230', the button 236' transitions or toggles from a configuration to the next configuration.

In one embodiment configured with three powered configurations, the button 236' is in communication with the motor 206', via the processor 235', and controls the rotational speed produced by the motor 206' based on the configuration of the button 236'. When the button 236' is in the off configuration, then the motor 206' is off and does not rotate the macerating element 400'. When the button 236' is in the low configuration, the motor 206' is on and rotates the macerating element 400' in a range between 500 rpm and 5,000 rpm. When the button 236' is in the high configuration, the motor 206' is on and rotates the macerating element 400' in a range between 1,000 rpm and 10,000 rpm. Other ranges and set points for each configuration are likewise within the scope of this disclosure.

In certain embodiments, as also noted above, the handle 200' may be configured with variable speed control. For example, the amount of pressure the user applies to the trigger 230' may determine the speed of the macerating element 400'. The more pressure applied to the trigger 230' by the user may thus correlate with an increase in the rotational speed of the macerating element 400'.

The rotational speed control mechanism may also comprise a sensor 237' configured to detect the current rotational speed produced by the motor 206'. The sensor 237' is configured to detect the rotation of magnets that rotate at the same speed as the macerating element 400'. The illustrated embodiment illustrates two magnets 238' and 239' that rotate about an axis A1 at the same speed as the macerating element 400'. Further, in the illustrated arrangement, the rotation of the magnets 238' and 239' is detected by the sensor 237'. In some embodiments, the sensor 237' is configured to detect the magnets 238' and 239' when the sensor 237' is within a close proximity of the magnets 238' and 239'. Thus, as the magnets 238' and 239' rotate (and thus change in proximity with respect to the sensor 237') the sensor 237' output may be correlated to a rotational speed. The sensor 237' may communicate with the processor 235' of the rotational speed control mechanism to inform the processor 235' of the current speed of the macerating element 400'.

The processor 235' may further include logic configured to maintain the speed of the macerating element 400' at selected speed. For example, if the button 236' is disposed in the low configuration, and the speed of the low configuration equates to 5,000 rpm, the processor 235' may determine the rotational speed of the macerating element 400' via the sensor 237' by sensing the rotational speed of the magnets 238' and 239'. If the rotational speed is below or above the predetermined speed (based on the configuration of the button 236'—in the case of the present example, 5,000 rpm), the processor 235' may send instructions to the motor 206' to either increase or decrease power input to the motor and, thus, the rotational speed produced by the motor 206'.

In some embodiments, the handle 200' comprises an indicator 228' that indicates the configuration the button 236'. In some embodiments, the indicator 228' may be an LED light that changes colors based on the configuration of the button 236'. For example, the LED may be a blue light when the button 236' is in the low configuration and may be a green light when the button 236' is in the high configuration, and may be off when the button 236' is in the off configuration.

During some therapies, the macerating element 400' encounters the blockage 20 to macerate, as seen in FIGS. 10-13. When the macerating element 400', e.g., the expandable basket 410', macerates the blockage 20, the rotation of the macerating element 400' may be decreased due to the resistance encountered by the macerating element 400'. In some instances, the sensor 237' may be configured to detect the decrease in the rotation of the macerating element 400' via the rotation of the magnets 238' and 239' and the processor 235' may then send instructions to the motor 206' to increase power input to the motor 206'. Similarly, after the macerating element 400' has completely macerated the blockage 20, the rotational speed of the macerating element 400' may increase over the predetermined rotational speed due to the lack of resistance and the power input to the motor 206'. The processor 235' may then decrease power input to the motor 206' to decrease the rotation speed until the macerating element 400' reached its predetermined rotational speed. Thus, the sensor 237' and processor 235' may be configured to automatically maintain a set rotational speed during use.

The handle 200' may further include a diameter control mechanism for controlling the diameter of the expandable basket 410'. The diameter control mechanism may be a slider 240' that enables the user to slide the slider 240' horizontally to variably control the diameter of the expandable basket 410'. The user may manipulate the diameter control mechanism to set the diameter of the expandable basket 410' during a macerating procedure. For example, if the user knows that the clot or blockage 20 is disposed within a specific vessel with a specific diameter, the user may manipulate the control mechanism to lock the maximum diameter of the expandable basket 410' at a diameter that is less than the diameter of the vessel to avoid damaging the vessel during the macerating procedure.

As discussed above, the slider 240' may include a plurality of detents. The detents may lock the slider 240' in place until a predetermined amount of force is applied to the slider 240' to release it from the detent until it reaches the next detent.

In other embodiments, the slider 240' may utilize a spring system 242' to control the sliding of the slider 240' along a slide track 244'. The position of the slider 240' along the slide track 244' determines the diameter of the expandable basket 410'. The spring system 242' is configured to bias the slider 240' toward the housing 210' and against a plurality of pads 246' disposed on the inner surface of the housing 210'. The user may apply force greater than the spring system 242' to detach the slider 240' from the housing 210' and the plurality of pads 246'. Once the slider 240' is detached, the user may slide the slider 240' along the slide track 244' to set the diameter of the expandable basket 410'.

In some embodiments, the plurality of pads 246' comprise a coefficient of friction that is greater than the coefficient of the housing 210'. The plurality of pads 246' may extend along the slide track 244'. When the user does not apply a force to the slider 240', the spring system 242' biases an undercarriage 241' of the slider 240' against the plurality of pads 246' to prevent undesired movement of the slider 240'. In some embodiments, the plurality of pads 246' is silicone.

In other embodiments, the plurality of pads 246' may be coupled to the undercarriage 241' of the slider 240' rather than coupled to the housing 210' as shown in FIG. 15 and as described above. In some such embodiments, the plurality of pads 246' may be disposed between the undercarriage 241' and the housing 210'. Accordingly, the plurality of pads 246' may be in contact with the housing 210' until a user applies a force greater than the spring system 242' to detach the slider 240' from the housing 210', enabling the user to horizontally slide the slider 240'. The plurality of pads 246' may thus prevent inadvertent sliding of the slider 240' when the undercarriage 241' and the plurality of pads 246' are in contact with the housing 210'.

In some embodiments, the undercarriage 241' may be fabricated from a material that comprises a coefficient of friction that is greater than the coefficient of the housing 210'. In some such embodiments, the undercarriage 241' may thus be configured to help prevent inadvertent sliding of the slider 240'.

The handle 200' may be designed to fit ergonomically within the hand of the user, i.e., a handheld device. The handle 200' may include the distal portion 202' and the proximal portion 204'. The proximal portion 204' may be slightly angled relative to the distal portion 202', enabling the user to grip the proximal portion 204' with their palm and still manipulate the trigger 230' and the slider 240' with their thumb and fingers. For example, the user could manipulate the trigger 230' with their thumb and manipulate the slider 240' with their index finger.

The handle 200' may further include a second port 250'. The second port 250' may communicate with a lumen disposed within the macerating element 400'. The user may advance the guidewire 500' through the second port 250' and the lumen of the handle 200' and through the first port 220' to the lumen of the macerating element 400'. The second port 250' may be in fluid communication with the lumen of the macerating element 400'. The second port 250' may function as an aspiration pump for infusion medication, saline, etc. For example, the user may infuse a medication, such as tPA, to help break up the clot or blockage 20 before the user attempts to macerate the clot or blockage 20. In some embodiments, a vacuum source may be applied to the second port 250' to remove the macerated clot or blockage 20.

The handle 200' may further include a third port 260'. The third port 260' may communicate with another lumen disposed within the catheter 300' between the macerating element 400' and the catheter 300'. The third port 260 may also function as an aspiration pump or infusion pump. In some embodiments, a vacuum source may be applied to the third port 260' to remove the macerated clot or blockage 20. In some embodiments, the user may infuse a medication, such as tPA, to help break up the clot or blockage 20.

In some embodiments, the handle 200' may further include a fourth port 270'. The fourth port 270' may communication with a lumen disposed within the catheter 300'. This lumen may the same lumen discussed above for the first port 220', the second port 250', or the third port 260'. Similar to the other pots, the fourth port 270' may function as an aspiration pump or an infusion pump. In some embodiments, a vacuum source may be applied to the fourth port 270' to remove the macerated clot or blockage 20.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A macerating element for macerating a blockage or clot, comprising:
   a catheter;
   a tubular shaft comprising a distal end and a proximal end;
   an expandable basket disposed at the distal end of the tubular shaft, wherein the expandable basket comprises a plurality of struts that form a braiding pattern, wherein the expandable basket is configured to rotate to macerate the blockage or clot, and wherein the braiding pattern of the expandable basket comprises a picks per inch that ranges from 2 to 10;
   an outer tubular shaft that extends the length of the catheter and is disposed around the tubular shaft and within the catheter, the outer tubular shaft formed from the plurality of struts of the expandable basket, wherein the outer tubular shaft comprises a transition point where a picks per inch of the outer tubular shaft transition from the picks per inch of the outer tubular shaft to the picks per inch of the expandable basket, and wherein the picks per inch of the outer tubular shaft ranges from 16 to 40;
   a first port for aspiration and/or infusion;
   a second port for aspiration and/or infusion; and a third port for aspiration and/or infusion, wherein the tubular shaft comprises a lumen that extends from the proximal end to the distal end and is in fluid communication with the first port,
   wherein a second lumen is disposed between the tubular shaft and the outer tubular shaft and is in fluid communication with the second port,
   wherein a third lumen is disposed between the outer tubular shaft and the catheter and is in fluid communication with the third port, and wherein the plurality of struts comprise a flattened configuration with rounded edges.

2. The macerating element of claim 1, wherein the diameter of the expandable basket in a collapsed configuration ranges from 1 mm to 5 mm, and wherein the diameter of the expandable basket in an expanded configuration ranges from 5 mm to 30 mm.

3. The macerating element of claim 1, wherein the expandable basket comprises 12-18 struts.

4. The macerating element of claim 1, wherein the outer tubular shaft and the tubular shaft move axially relative to each other, and wherein axial movement of the outer tubular shaft and the tubular shaft in relation to each other is configured to expand and collapse the expandable basket.

5. A macerating system for macerating a blockage or clot, comprising:
 a handle;
 a catheter that extends from a distal end of the handle; and
 a macerating element partially disposed within the catheter comprising:
  a tubular shaft comprising a distal end and a proximal end;
  an expandable basket disposed at the distal end of the tubular shaft, wherein the expandable basket is configured to rotate to macerate the blockage or clot, wherein the expandable basket comprises a plurality of struts that form a braiding pattern, wherein the braiding pattern of the expandable basket comprises a picks per inch that ranges from 2 to 10, and wherein the braided pattern is a half load braiding pattern; and
  an outer tubular shaft that is disposed around the tubular shaft, the outer tubular shaft formed from the plurality of struts of the expandable basket, wherein a distal end of the outer tubular shaft is coupled to the expandable basket, wherein the outer tubular shaft comprises a transition point where a picks per inch of the outer tubular shaft transition from the picks per inch of the outer tubular shaft to the picks per inch of the expandable basket, and wherein the picks per inch of the outer tubular shaft ranges from 16 to 40.

6. The macerating system of claim 5, wherein the handle comprises a diameter control mechanism for controlling the diameter of the expandable basket during a procedure.

7. The macerating system of claim 6, wherein the diameter control mechanism comprises a slider that slides along a slider track, wherein the position of the slider along the slider track determines the diameter of the expandable basket.

8. The macerating system of claim 7, wherein the slider engages with a plurality of pads that are disposed within a housing along the slider track, wherein the plurality of pads comprise a greater coefficient of friction than the housing to prevent unintentional movement of the slider along the slider track.

9. The macerating system of claim 5, wherein the handle comprises a rotational speed control mechanism for controlling the rotational speed of the expandable basket.

10. The macerating system of claim 9, wherein the rotational speed control mechanism comprises a sensor for measuring the angular velocity of the expandable basket.

11. The macerating system of claim 10, further comprising a plurality of magnets that rotate at the same angular velocity as that of the expandable basket, wherein the sensor is configured to measure the angular velocity of the plurality of magnets to determine the angular velocity of the expandable basket.

12. The macerating system of claim 11, wherein the rotational speed control mechanism comprises three configurations, an off configuration wherein the angular velocity of the expandable basket is zero, a low configuration wherein the angular velocity of the expandable basket is between 500 and 5,000 rpm, and a high configuration wherein the angular velocity of the expandable basket is between 1,000 and 10,000 rpm.

13. The macerating system of claim 12, wherein the rotational speed control mechanism further comprises an indicator to indicate the configuration of the rotational speed control mechanism.

14. The macerating system of claim 12, wherein the rotational speed control mechanism comprises a processor that communicates with a motor that rotates the expandable basket, wherein the processor further communicates with the sensor, wherein the processor is configured to increase or decrease the angular velocity produced by the motor to increase or decrease the angular velocity of the expandable basket based on the angular velocity determined by the sensor.

\* \* \* \* \*